(12) United States Patent
Bjorge (10) Patent No.: US 7,811,248 B2
(45) Date of Patent: Oct. 12, 2010

(54) SUPPORT DEVICE FOR A BREAST PUMP

(76) Inventor: Tammy Bjorge, 1300 Alps Dr., McLean, VA (US) 22102

( * ) Notice: Subject to any disclaimer, the term of this patent is extended or adjusted under 35 U.S.C. 154(b) by 0 days.

(21) Appl. No.: 11/835,156

(22) Filed: Aug. 7, 2007

(65) Prior Publication Data

US 2008/0039781 A1 Feb. 14, 2008

Related U.S. Application Data

(60) Provisional application No. 60/821,748, filed on Aug. 8, 2006.

(51) Int. Cl.
*A61M 1/06* (2006.01)
(52) U.S. Cl. .............. 604/74; 450/36; 450/60; 450/63; 450/68; 2/267
(58) Field of Classification Search ............. 604/73, 604/74, 75, 76; 450/36–37, 60, 63, 65, 67–68, 450/77, 78; 2/267
See application file for complete search history.

(56) References Cited

U.S. PATENT DOCUMENTS

| 2,555,086 | A | * | 5/1951 | Guinn | 604/333 |
|---|---|---|---|---|---|
| D213,078 | S | * | 12/1968 | Katzman et al. | D24/206 |
| 4,473,370 | A | * | 9/1984 | Weiss | 604/402 |
| 4,850,376 | A | * | 7/1989 | DellaVecchia et al. | 128/858 |
| 4,898,162 | A | * | 2/1990 | Worthrich | 128/888 |
| 5,230,335 | A | * | 7/1993 | Johnson et al. | 607/104 |
| 5,235,974 | A | * | 8/1993 | Miller | 607/108 |
| 5,514,166 | A | * | 5/1996 | Silver et al. | 604/74 |
| 5,572,740 | A | * | 11/1996 | Geniesse | 2/46 |
| 5,575,768 | A | * | 11/1996 | Lockridge et al. | 604/74 |
| 5,643,184 | A | * | 7/1997 | Toso | 602/19 |
| 5,679,052 | A | * | 10/1997 | Rucki | 450/57 |
| 5,897,580 | A | * | 4/1999 | Silver | 607/108 |
| 6,027,396 | A | * | 2/2000 | Yonchar | 450/36 |
| 6,213,840 | B1 | | 4/2001 | Han | |
| 6,227,936 | B1 | | 5/2001 | Mendoza | |
| 6,247,996 | B1 | * | 6/2001 | Fields | 450/36 |
| 6,261,313 | B1 | * | 7/2001 | MacWhinnie et al. | 607/108 |
| 6,358,226 | B1 | * | 3/2002 | Ryan | 604/74 |
| 6,379,327 | B2 | * | 4/2002 | Lundy | 604/74 |
| 6,390,886 | B1 | * | 5/2002 | Roberts | 450/37 |
| 6,659,841 | B2 | | 12/2003 | Raimondo | |
| 6,705,920 | B1 | * | 3/2004 | Engel | 450/36 |
| 6,764,377 | B2 | | 7/2004 | Gillan | |
| 6,866,558 | B2 | * | 3/2005 | Luciano et al. | 450/36 |
| 2003/0003844 | A1 | * | 1/2003 | Jones et al. | 450/88 |
| 2003/0167037 | A1 | * | 9/2003 | Fialkoff | 604/74 |
| 2003/0191427 | A1 | * | 10/2003 | Jay et al. | 604/24 |
| 2003/0191433 | A1 | * | 10/2003 | Prentiss | 604/74 |
| 2005/0070817 | A1 | * | 3/2005 | Mueller, Jr. | 600/563 |
| 2006/0243286 | A1 | * | 11/2006 | Durette | 128/858 |

* cited by examiner

*Primary Examiner*—Nicholas D Lucchesi
*Assistant Examiner*—Quynh-Nhu H Vu
(74) *Attorney, Agent, or Firm*—Edell, Shapiro & Finnan, LLC (57) ABSTRACT

A device that supports a breast pump in a "hands-free" manner is disclosed. The device includes a cover with an opening and strap that connects the cover to an article of clothing such as a nursing bra. When connected, the device securely orients a breast shield of a breast pump over the breast of a user.

11 Claims, 6 Drawing Sheets

Figure 1:
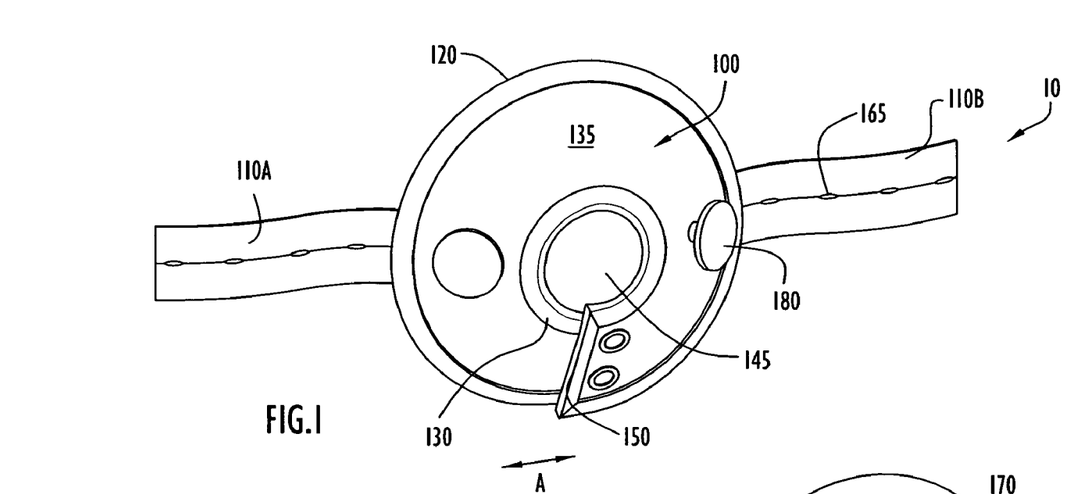
FIG. 1 is a front perspective view of the support device in accordance with an embodiment of the present invention.

FIG.9 though embodiments of the present invention. As illustrated, the support device 10 includes a body or support member 100 (also called a cover) and connection system. The body 100 is operable to couple to and support a breast pump on a user. The body 100 has a distal base portion 120 and a proximal upper portion 130, as well as a front surface 135 and a rear surface 140. The shape of the body is not particularly limited. By way of example, the body 110 may possess a generally annular shape including an opening or port 145. The port may possess dimensions (e.g., a diameter) sufficient to permit the passage of the flange of a breast shield therethrough. The port 145 exposes the mother's nipple while simultaneously allowing the breast shield of the pumping device to pass through the body 100. By way of further example, the body 100 may possess a generally frusto-conical shape, with the rear surface 140 of the body being generally contoured with the outer surface of a breast shield. With this configuration, the body 100 securely cradles the shield, i.e., the shield is at least partially nested within the body such the translational movement of the shield with respect to the body is prevented.

SUPPORT DEVICE FOR A BREAST PUMP

CROSS REFERENCE TO RELATED APPLICATIONS

This application is a nonprovisional of U.S. Provisional Application No. 60/821,748 entitled "Support Device for a Breast Pump" and filed on 8 Aug. 2006, the disclosure of which is hereby incorporated by reference in its entirety.

FIELD OF THE INVENTION

The present invention relates to a hands-free breast-pump accessory and, in particular, to a device for supporting the shield of a breast pump over the breast of a user.

BACKGROUND OF THE INVENTION

A woman who is nursing an infant typically will express breast milk to store for times when she is unable or unavailable to breast feed her infants. Breast pumps are used to express and store breast milk for later use. Two types of breast pumps are generally available: motor-driven pumps and manually-operated pumps. These pumps typically include a funnel-shaped cup (called a breast shield) that fits over the nipple (and a substantial portion of the breast), a vacuum pump (e.g., manually driven piston cylinder, squeeze bulb, or electrically driven vacuum device) that generates an intermittent vacuum in the breast cup, and a container for the expressed breast milk. The intermittent suction generated by the vacuum pump within the breast cup causes a pulling or pressing of the breast, which is intended to mimic an infant's suckling action, thereby expressing milk. The collection container, such as a small milk bottle, is ordinarily connected to the breast cup through an intermediate milk-directing channel and valve arrangement. The expressed milk typically flows from the breast cup to the collection container for storage. In use, a woman expresses her milk by using the electric or manual pumping device in conjunction with the shield, which the woman holds tightly against her nipple to create suction and to direct the flow of milk into a storage container.

Clothing has been adapted to simplify the task of breast feeding. For example, nursing brassieres include a bra cup with a flap that is unfastened to partially expose a breast, enabling nursing or the collection of breast milk through pumping. Similarly, shirts such as tank tops often include a panel that is unfastened to expose one or both breasts.

Such clothing, while helpful, does not remedy the work intensive nature of pumping. When using the breast pump, the mother must manually hold the breast cup over the exposed portion of the breast. Due to the length of time required to express milk when using a pump, a woman oftentimes expresses both breasts simultaneously. To express both breasts, the woman must hold a funnel with each hand against her breasts, leaving her an awkward position, as well as unable to enjoy other activities. As a result, the nursing mother will not have the full use of both hands to perform other tasks. Therefore, it would be advantageous to develop a method and device that will permit a mother to use a conventional breast pump while also allowing her the free use of her hands to perform other tasks.

SUMMARY OF THE INVENTION

The present invention is directed toward a device that supports a breast pump in a "hands-free" manner. The device includes a body and a connection member operable to secure the body to an article of clothing such as a nursing bra. In operation, the device couples to the article of clothing, securely orienting the shield of a breast pump over the breast of a user.

BRIEF DESCRIPTION OF THE DRAWINGS

Like reference numerals have been used to identify like elements throughout this disclosure.

DETAILED DESCRIPTION OF THE INVENTION

FIG. 1 shows a support device 10 in accordance with an embodiment of the present invention. As illustrated, the support device 10 includes a body or support member 100 (also called a cover) and connection system. The body 100 is operable to couple to and support a breast pump on a user. The body 100 has a distal base portion 120 and a proximal upper portion 130, as well as a front surface 135 and a rear surface 140. The shape of the body is not particularly limited. By way of example, the body 110 may possess a generally annular shape including an opening or port 145. The port may possess dimensions (e.g., a diameter) sufficient to permit the passage of the flange of a breast shield therethrough. The port 145 exposes the mother's nipple while simultaneously allowing the breast shield of the pumping device to pass through the body 100. By way of further example, the body 100 may possess a generally frusto-conical shape, with the rear surface 140 of the body being generally contoured with the outer surface of a breast shield. With this configuration, the body 100 securely cradles the shield, i.e., the shield is at least partially nested within the body such the translational movement of the shield with respect to the body is prevented.

Figure 2:
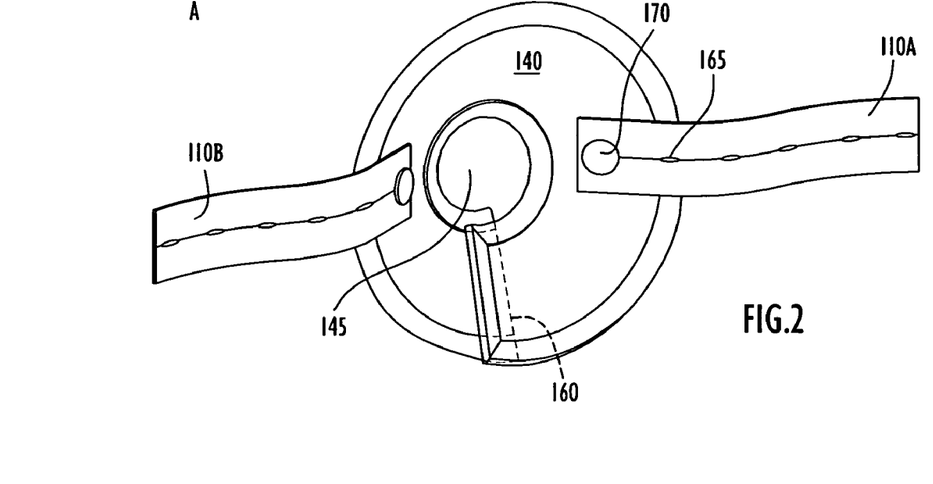
FIG. 2 is a rear perspective view of the support device shown in FIG. 1.

The body 100 may have a unitary structure, fixing the dimensions of the body and/or port 145. Alternatively, the body 100 may include ends that are moveable with respect to each other, enabling a user to adjust the dimensions the body and/or port 145. As seen best in FIG. 2, the body 100 may include a first terminal end 150 and a second terminal end 160. The body 100 may be sufficiently flexible to permit the relative movement of the ends 150, 160. In addition, the first end 150 may overlap the second end at varying degrees. With this configuration, translating the first end 150 with respect to the second end 160 (indicated by arrow A) alters the dimensions of the body 100. For example, moving the first end 150 from a first position to a second position this alters the diameter of the port 145 (either increasing or decreasing the diameter). This, in turn, accommodates various breast shield flange sizes.

Figure 9:
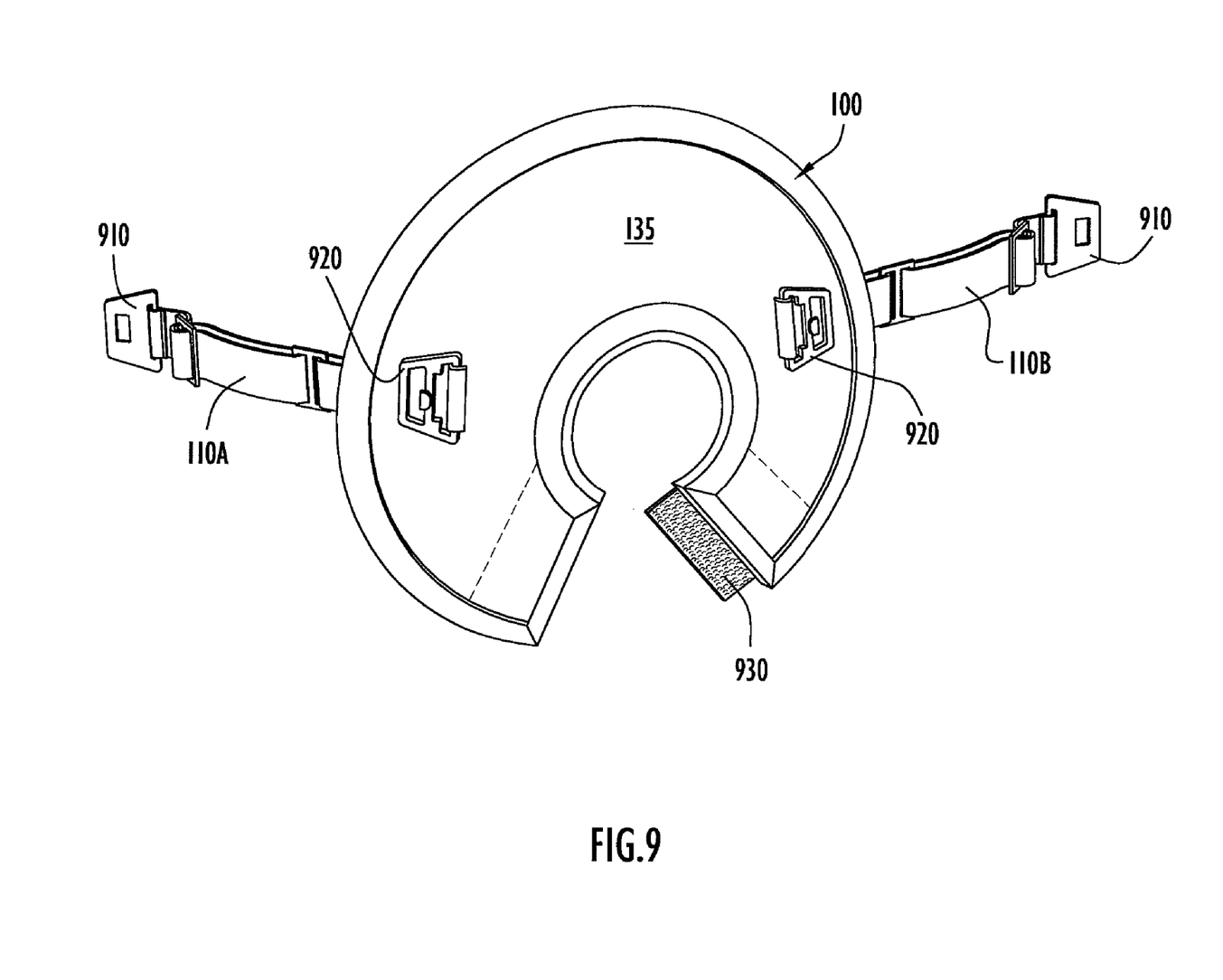
FIG. 9 illustrates a front perspective view of a support device in accordance with another embodiment of the invention.

Once the proper port diameter is achieved, the ends 150, 160 of the body 100 may be secured via fastening system. By way of example, the first end 150 may include a series of hooks operable to mate with eyes formed on the second end 160. Alternatively, as shown in FIG. 9, the ends 150, 160 may include a hook and loop fastener (e.g., VELCRO). It is important to note that the fastener system is not limited so long as it permits the connection and/or separation of the first end 150 and the second end 160. Thus, the fastening system includes, but is not limited to, buttons, snaps, buckles, strings, etc.

The body 100 may be formed from any material suitable for its described purpose. By way of example, the material may include, but is not limited to, flexible material such as natural and synthetic fabric (cotton, RAYON, LYCRA, NYLON, etc.). In addition, the cover may also be formed from stiffer (more rigid) materials that are less conforming, but provide more structure, such as foam, plastic, rubber, latex, or other similar materials. The body 100, furthermore, may include reinforcing wire, etc. to stabilize the structure. For example, the port 145 may include reinforcing wire to provide a structurally sound attachment point for the breast shield of the breast pump.

The connection system may be configured to couple the body 100 to an article of clothing. The connection system may include one or more connection members. In the embodiment illustrated, the connection system includes a first connection member 110A and a second connection member 110B. The connection members 110A, 110B may be in the form of straps, ties, bands, etc. By way of specific example, the connection members may comprise a first strap 110A and a second strap 110B made of pliable material. The material forming the straps may include, but is not limited to, cloth, elastic material, leather, cotton, RAYON, LYCRA, NYLON, etc. The connection members 110A, 110B may be secured to the body 100 utilizing sewing, fasteners (e.g., buttons, buckles, and snaps), etc. The connection members 110A, 110B may be permanently attached to the body 100, or may be removably attached to the body. In the embodiment of FIG. 1, the connection members 110A, 110B include one or more slots 165 that selectively mate with a first attachment point 170 disposed on the rear surface 140 of body 100 and a second attachment point 180 disposed on the front surface 135 of the body. By way of example, the attachment points 170, 180 may include buttons configured to mate with the slots 165 on the connection members 110A, 110B. With this configuration, the length of the connection member 110A, 110B may be adjusted (i.e., the distance the outer end of the strap extends from the perimeter of the body 100 may be selectively altered) to accommodate clothing of various configurations (e.g., nursing bras, tank tops, etc.).

Alternatively or in addition to, the connection system may also include a first mating connector and a second mating connector that releasably mates with the first connector. For example, the connectors may include complementary portions (male and female) of a buckle. Referring to FIG. 9, the device 10 includes the first connection member 110A and the second connection member 110B. Each connection member 110A, 110B may have a proximal end connected (e.g., by sewing) to the body 100 (e.g., to either the front surface 135 or the rear surface 140) and a distal end connected to a first mating connector 910. A second mating connector 920, configured to mate with the first mating connector 910, may be connected (e.g., sewn) to the body 100 (e.g., to either the front surface 135 or the rear surface 140).

Figure 3:
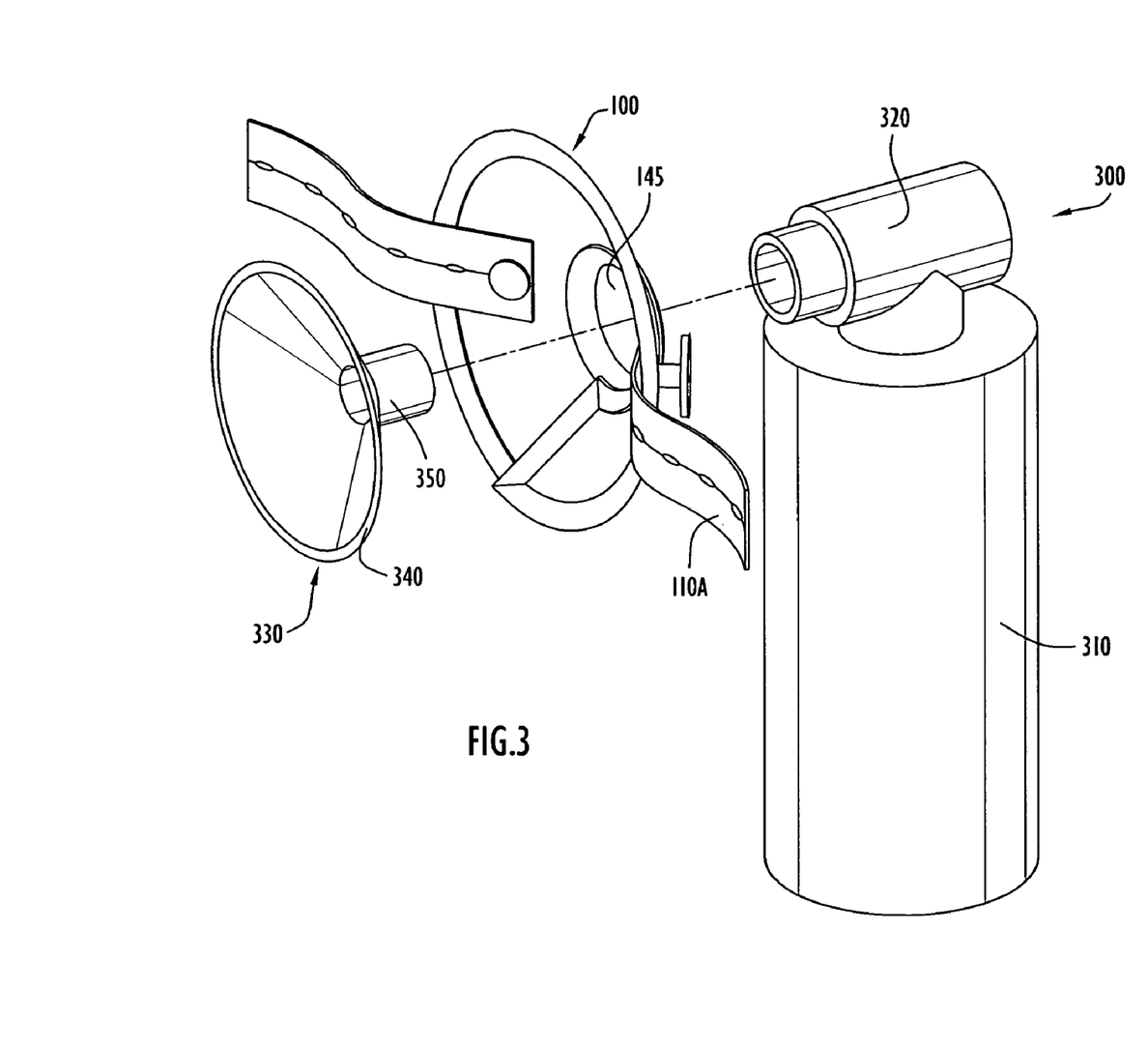
FIG. 3 is an exploded view of the support device shown in FIG. 1 and a breast pump.
Figure 4:
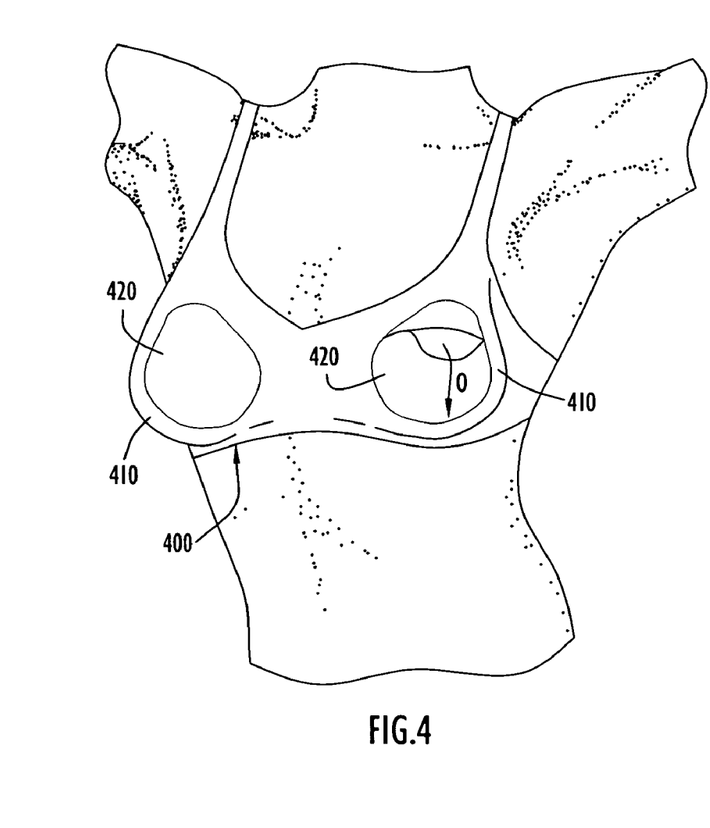
FIGS. 4-7 illustrate the connection of the support device shown in FIG. 1 to a nursing bra.
Figure 5:
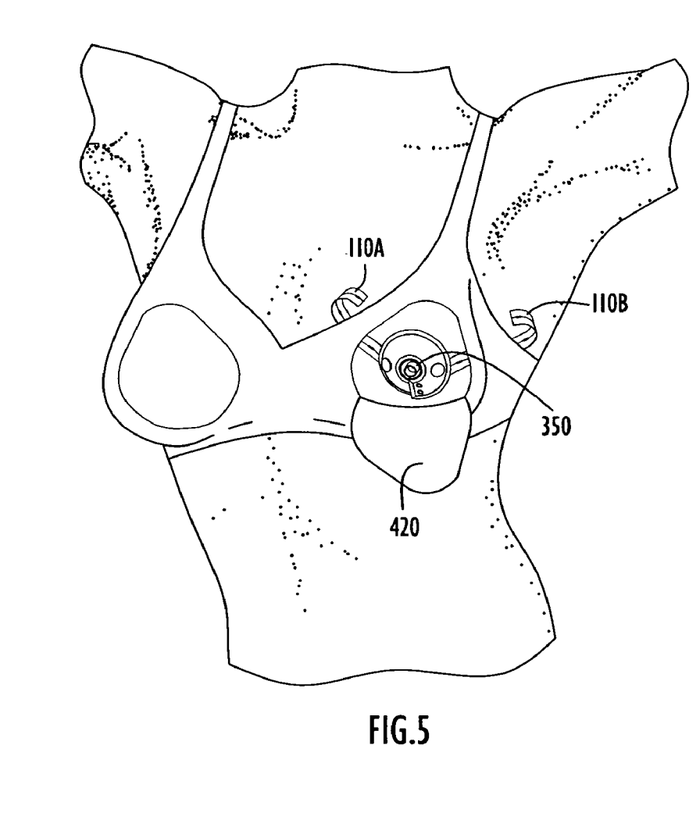

FIG. 3 illustrates an exploded view of the support device 10 and a breast pump 300. As illustrated, the breast pump 300 includes a container 310, a pump 320, and a breast shield 330 having a funnel 340 and a flange or base 350. The flange 350 of the breast shield passes through the port 145 of the body 100 and connects to the pump 320. The ends 150, 160 of the body 100 may then be adjusted to snugly secure the port 145 around the flange 350 of the shield 330 as described above. In addition, the rear surface 140 of the body 100 may be contoured with the exterior surface of the shield 330, permitting the nesting of the shield 330 within the body 100.

It is important to note that while a breast shield 330 that is detachable from the pump 320 is illustrated, a breast pump 300 including a permanently attached shield 330 may be utilized with the support device 10. To connect the body 100 to the shield, the ends 150, 160 are simply be separated to create an opening sufficient to permit the passage of the shield 330 (i.e., the flange 350) between the ends and into the port 145, and then securing the ends shut via the fastening system.

Figure 6:
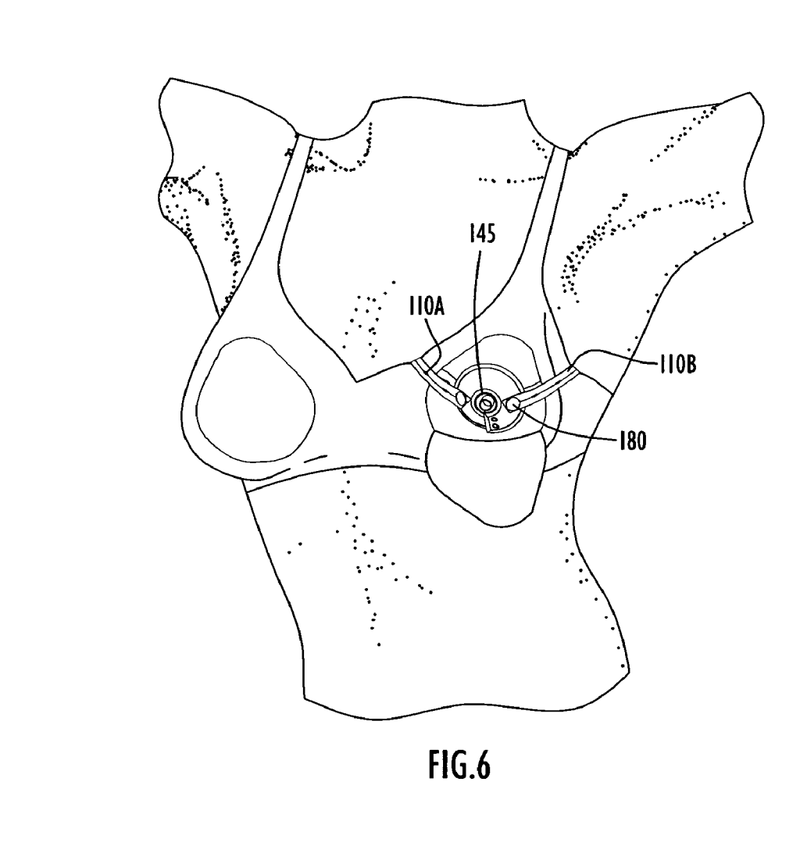
Figure 7:
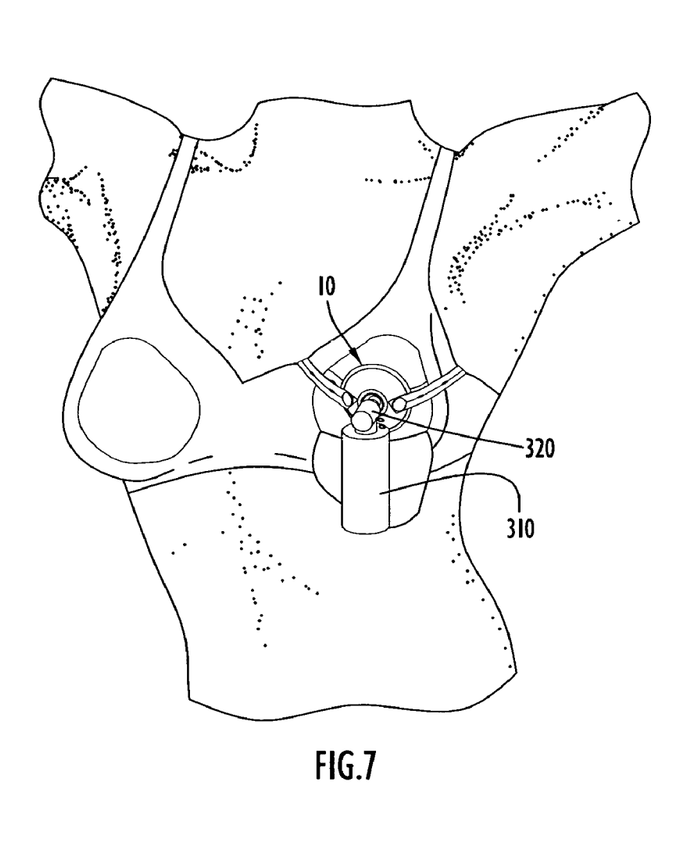

The operation of the support device is further explained with reference to FIGS. 4-7. FIG. 7 illustrates a front perspective view of a user wearing a nursing bra 400. Initially, the breast shield 330 may be nested within the body 100 as described above, with the flange 350 of the shield 330 passing through the port 145. Each cup 410 of the bra 400 may include a flap 420 that is selectively opened (indicated by arrow O) to provide access to the nipple. To connect the support device 10 to the bra 400, the flap 420 is opened (FIG. 4) and the body 100 is oriented over the breast such that the port 145 is generally positioned over the nipple. The connection members 110A, 110B (already connected to rear attachment point 170) are drawn/looped around the cup 410 (FIG. 5) and connected to the front attachment point 180 (FIG. 6). The connection members 110A, 110B are selectively secured to the front attachment points 180 such that the body 100 is snug against the breast. Referring to FIG. 7, the pump 320 of breast pump 300 may then be connected to the flange 350 of the shield 330. The user may then activate the pump to express and store the breast milk.

Figure 8:
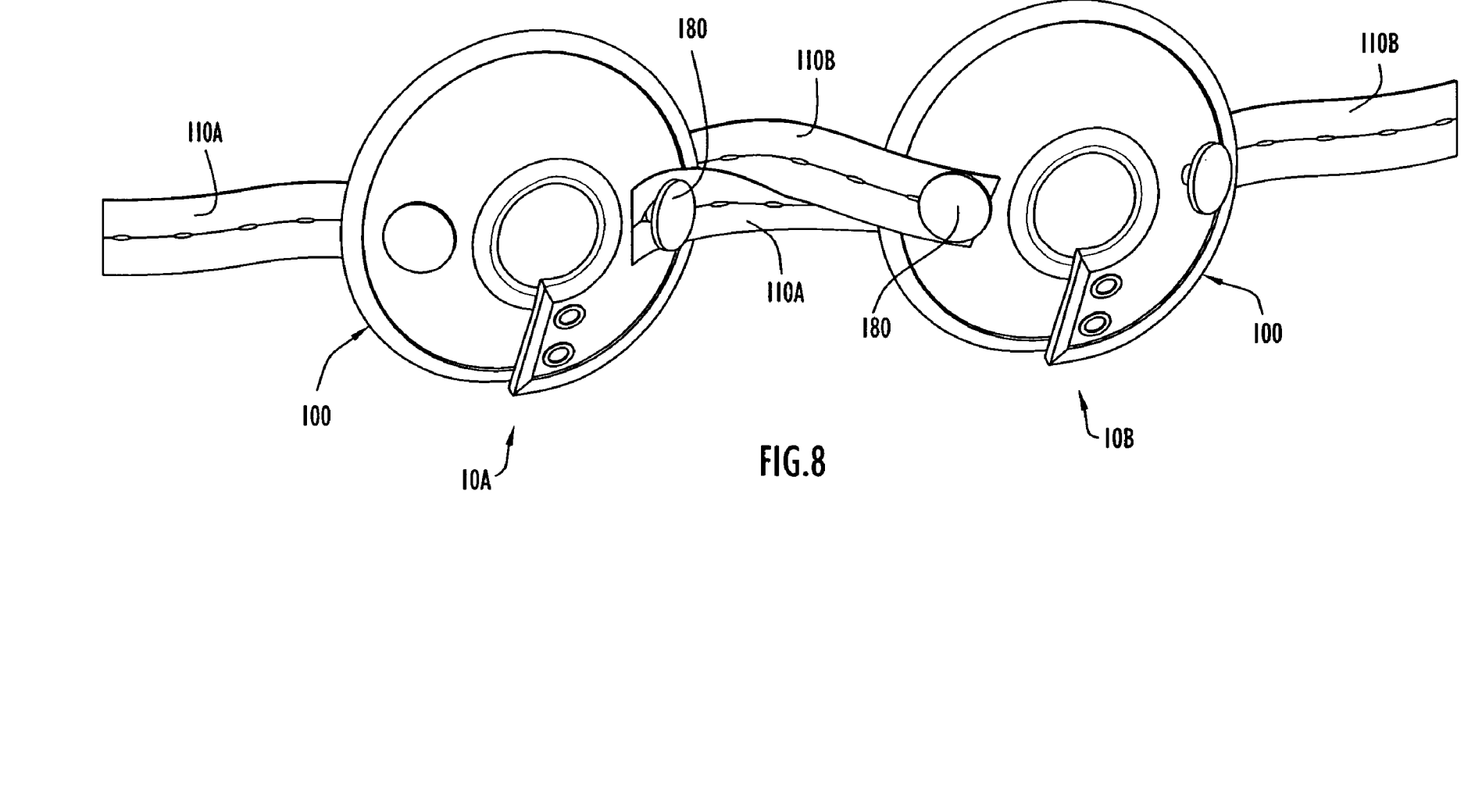
FIG. 8 illustrates is a front perspective view of a pair of the support devices shown in FIG. 1, showing the coupling of multiple devices together.

If a second breast pump is desired, the process is repeated with a second support device 100 over the opposite breast/bra cup 410. Alternatively, the support device may be configured to permit the simultaneous expression of milk from both breasts. FIG. 8 illustrates a front perspective view of a pair of support devices 10A, 10B coupled together. With this configuration, the outer connection members (the first connection member 110A of a first device 10A and the second connection member of a second device 10B) connect to an article of clothing as described above. In addition, the inner connection members may be fastened to the adjacent device. Specifically, the second connection member 110B of the first device 10A may connect to the front attachment point 180 of the second device 10B. Similarly, the first connection member 110A of the second device 10B may connect to the front attachment point 180 of the first device 10B. In this manner, the inner connection members form a bridge to support devices 10A, 10B.

As should be understood, the support device 10 may first be connected to the nursing bra 400, and then the breast pump 300 connected thereto. Such a procedure is particularly advantageous when a breast pump including a permanently attached breast shield is used.

With the above configuration, the support device 10 operates to support a breast pump on an exposed breast such that the breast pump is held in place without requiring additional support from the user. In addition, the configuration does not require the use of anchoring members integrated into the article of clothing. That is, the article of clothing does not have anchoring members (loops, supports, etc.) attached to the garment to which the body must couple in order to be secured to the article of clothing. Instead, support device 10 directly connects to a portion of the user's clothing (nursing brassiere, tank top, etc). The present invention permits a nursing mother to use a breast pump to collect and store breast milk, while also providing her with free use of her hands to perform other jobs, tasks, or chores. In addition, the present invention allows for hands-free "double pumping". The present invention, furthermore, is simple to use and allows the breast pump to be quickly and firmly supported on the exposed breast.

As discussed above, FIG. 9 is a front perspective view of a support device 10 in accordance with another embodiment of the invention. In addition to the connection system including a first connector 910 and the second connector 920, the fastening system configured to coupled the ends 150, 160 of the body together includes a hook and loop fastener 930.

While the invention has been described in detail and with reference to specific embodiments thereof, it will be apparent to one skilled in the art that various changes and modifications can be made therein without departing from the spirit and scope thereof. For example, the article of clothing is not particularly limited, and may include any clothing item to which the device 10 may connect. By way of specific example, although a nursing bra is illustrated, the article of clothing may also include nursing tops such as a shirt, a tank top, a sweater, etc. The article of clothing may further include dresses, nightwear, etc. The article of clothing may have any opening that provides access to the breast, such as front-only openings, two-piece look openings, side openings, cross-wrap openings, single center openings, all around openings, empire openings, inverted pleat openings, vested openings, built-in bra openings, etc.

The body 100 may be of any shape and possess any dimensions suitable for its described purpose (i.e., to fit around a woman's breast and receive a breast shield). The body 100 may also include a reinforcing material added to the outside or inside of the support device, or can be included in between various layers of the body. Similarly, the port 145 may be any shape and possess any dimensions suitable for its described purpose, and can be modified to accommodate various models of breast pump devices. The body 100 may further include a cap or panel configured to selectively cover the port 145. By way of example, the body 100 may comprise a panel that extends over the port 145. The panel may be connected to the body 100 such that it selectively opens to provide access to the opening (and thus the nipple).

The connection members 110A, 110B may be of any shape and possess any suitable dimensions. The length of the connection members 110A, 110B may be adjusted to allow the support device to be cinched to an existing nursing bra, and also allow for variation in breast size, pumping devices and general comfort. The attachment points 170, 180 may be disposed at any suitable location along the cover. The connection system to secure the ends of the connection members 110A, 110B (and thus the device 10 to a bra) is not particularly limited. In addition to the slot 165 and attachment points 170, 180, other mating fasteners may be used, including but not limited to, buttons, snaps, ties, stitching, zippers, hook-and-loop fasteners, buckles, etc.

For ease of illustration, the present invention is generally shown and described in terms of a single breast pump used for expressing breast milk from a single breast. However, it is specifically contemplated that the present invention is usable to support a breast pump on each of a woman's breasts for breast milk collection.

It is to be understood that terms such as "top", "bottom", "front", "rear", "side", "height", "length", "width", "upper", "lower", "interior", "exterior", and the like as may be used herein, merely describe points of reference and do not limit the present invention to any particular orientation or configuration. Thus, it is intended that the present invention covers the modifications and variations of this invention provided they come within the scope of the appended claims and their equivalents.

I claim:

1. A breast pump support device comprising:
   a frusto-conical body comprising:
   an interior surface and an exterior surface, the interior surface defining a breast-facing surface,
   a first opening oriented in spaced relation from a second opening,
   a wall including first and second terminal ends that extend the length of the body, wherein the first terminal end is selectively repositionable with respect to the second terminal end to alter a diameter of at least one of the first opening and the second opening, and
   a first mating connector secured to the exterior surface of the body; and
   a connection system configured to fasten the body to an article of clothing worn by a user, the connection system comprising a connection member having a proximal end and a distal end, wherein:
   the proximal end of the connection member is coupled to the body, and
   the distal end of the connection member comprises a second mating connector that releasably mates with the first mating connector,
   wherein the support device is configured to securely cradle a breast shield and prevent the translational movement of the shield when positioned within the body.

2. The support device of claim 1, wherein the device is fastened to an article of clothing is selected from the group consisting of a nursing bra, a nursing tank top, a nursing dress, and nursing nightwear.

3. The support device of claim 1, wherein the support device connects to the article of clothing without the use of an anchor disposed on the article of clothing.

4. The support device of claim 1, wherein:
   the first terminal end is configured to overlap the second terminal end; and
   the body further comprises a fastener operable to fasten the overlapping terminal ends of the body, securing the position of one terminal end with respect to the other terminal end.

5. The support device of claim 1 further comprising a breast shield disposed within the support device, the breast shield having a funnel section and a base section, wherein the breast shield is positioned in the body such that it contacts the interior surface and the base section extends through the first opening.

6. The support device of claim 1, wherein:
   the connection member extends from the body at an extension length; and
   the extension length of the connection member is selectively adjustable.

7. A support device for a breast pump comprising:
   a body configured to receive a breast shield having a funnel section and a base section, the body including a port permitting the passage of the base section of the breast shield therethrough, and wherein:
   the body comprises a wall defining a first opening oriented in spaced relation from a second opening, each opening possessing a diameter,
   the wall comprises first terminal end and a second terminal end, the ends running the length of the body, and the first and second ends are selectively repositionable with respect to each other to alter the diameter of at least one of the first opening and the second opening; and a connection system operable to fasten the body to an article of clothing, the connection system comprising:
 a first mating connector disposed on a front surface of the body,
 a first connection member comprising a proximal portion coupled to a rear surface of the body and a distal portion that connects to the first mating connector,
 a second mating connector disposed on a front surface of the body, and
 a second connection member comprising a proximal portion coupled to the rear surface of the body and a distal portion that connects to the second mating connector,
 wherein the distal portion of the first connection member comprises a third mating connector that connects to the first mating connector and the distal portion of the second connection member comprises a fourth mating connector that connects to the second mating connector, and wherein at least one of the first connection member and the second connection member extends from the rear body surface, passes through one of the first body opening and the second body opening, and to the front body surface, wherein the support device operatively positions the funnel portion over a breast of a user.

8. The support device of claim 7, wherein:
each connection member extends from the body at an extension length; and
the extension length of each connection member is selectively adjustable.

9. The support device of claim 7, wherein the body further comprises a fastener operable to selectively secure the position of the first terminal end with respect to the second terminal end.

10. A method of supporting a breast pump on a user, the method comprising:
(a) obtaining a breast pump including a breast shield having a base portion and a funnel portion;
(b) obtaining a support device comprising:
 a frusto-conical body comprising:
  an interior surface and an exterior surface, the interior surface defining a breast-facing surface,
  a first opening oriented in spaced relation from a second opening,
  a wall including first and second terminal ends that extend the length of the body, wherein the first terminal end is selectively repositionable with respect to the second terminal end to alter a diameter of at least one of the first opening and the second opening, and
  a first mating connector secured to the exterior surface of the body; and
 a connection system configured to fasten the body to an article of clothing worn by a user, the connection system comprising a connection member having a proximal end and a distal end, wherein:
  the proximal end of the connection member is coupled to the body, and
  the distal end of the connection member comprises a second mating connector that releasably mates with the first mating connector;
(c) positioning the breast shield within the support device; and
(d) securing the support device to the article of clothing such that support device orients the funnel portion over a breast of the user.

11. The method of claim 10, wherein:
the article of clothing comprises a bra including a cup with an opening covered by a removable flap; and
(d) further comprises (d.1) repositioning the flap to expose the breast and inserting the body into the opening.

* * * * *